United States Patent

Gull et al.

[11] Patent Number: 5,262,422
[45] Date of Patent: Nov. 16, 1993

[54] OCTAHYDROBENZO[G]QUINOLINE

[75] Inventors: Peter Gull, Pfeffingen, Switzerland; Rudolf Markstein, Rheinfelden, Fed. Rep. of Germany

[73] Assignee: Sandoz Ltd., Basel, Switzerland

[21] Appl. No.: 19,736

[22] Filed: Feb. 19, 1993

Related U.S. Application Data

[63] Continuation of Ser. No. 877,557, May 1, 1992, abandoned.

[30] Foreign Application Priority Data

May 2, 1991 [DE] Fed. Rep. of Germany ....... 4114325

[51] Int. Cl.$^5$ ................. A61K 31/435; C07D 401/12
[52] U.S. Cl. ...................... 514/290; 546/101
[58] Field of Search ........................ 546/101; 514/290

[56] References Cited

U.S. PATENT DOCUMENTS

| | | | |
|---|---|---|---|
| 4,147,789 | 4/1979 | Stutz et al. | 546/67 |
| 4,565,818 | 1/1986 | Nordmann et al. | 546/101 |
| 4,654,345 | 3/1987 | Cavanak | 514/250 |

OTHER PUBLICATIONS

Nordmann et al. J. Med. Chem., 28, 367–375, 1540–1542 (1985).

*Primary Examiner*—Donald G. Daus
*Attorney, Agent, or Firm*—Robert S. Honor; Melvyn M. Kassenoff; Thomas O. McGovern

[57] ABSTRACT

The invention relates to the compound of formula I

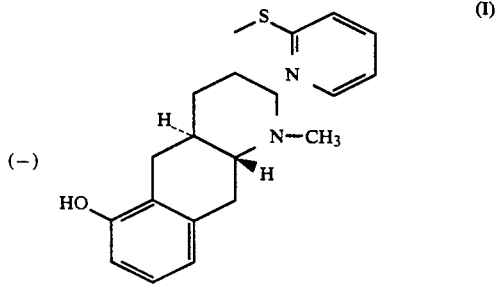

in free base form or in acid addition salt form its preparation and use as a medicament for glaucoma, depression, Morbus Parkinsonism or cocaine abuse.

6 Claims, No Drawings

OCTAHYDROBENZO[G]QUINOLINE

This is a continuation of application Ser. No. 07/877,557, filed May 1, 1992, now abandoned.

The present invention relates to a new octahydro[g-]quinoline, its production and its use in therapy.

The compound of the invention is the (−)−(3Oβ,4,α,β)-1,2,3,4,4a,5,10,10a-octahydro-3-[(2-pyridylthio)methyl]-1-methyl-6-hydroxy-benzo[g-]quinoline of formula I

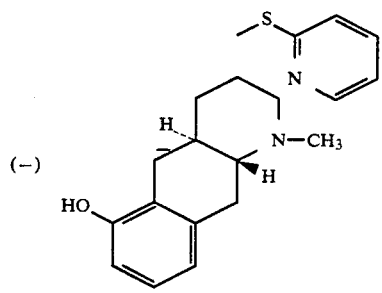

in free base form or in acid addition salt form.

Structurally related compounds are known from European Patent No. 77754. However, the compound of formula I has never been specifically disclosed. It has now surprisingly been found that this compound exhibits a particularly interesting pharmacological activity profile.

In accordance with the invention, the compound of formula I and its acid addition salts are obtained by methylating the compound of formula II

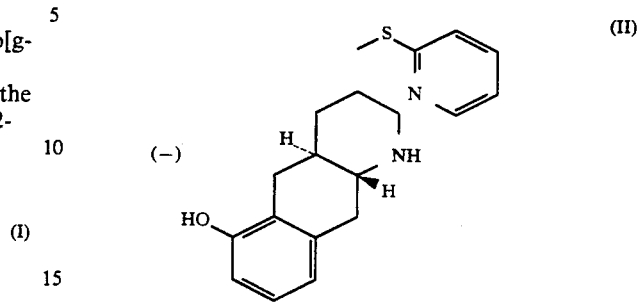

and if desired, converting the compound obtained into its acid addition salts.

The process according to the invention may be carried out by known methods, for example using formaldehyde/NaBH4, as described in the following example under e).

Working up of the reaction mixture obtained and purification of the compound of formula I thus produced may be carried out by known methods.

Acid addition salts can be produced from the free bases in known manner, and vice versa.

The starting compound of formula II may be prepared from the compound of formula VII in accordance with the following reaction scheme, for example as described in the example under a) to d):

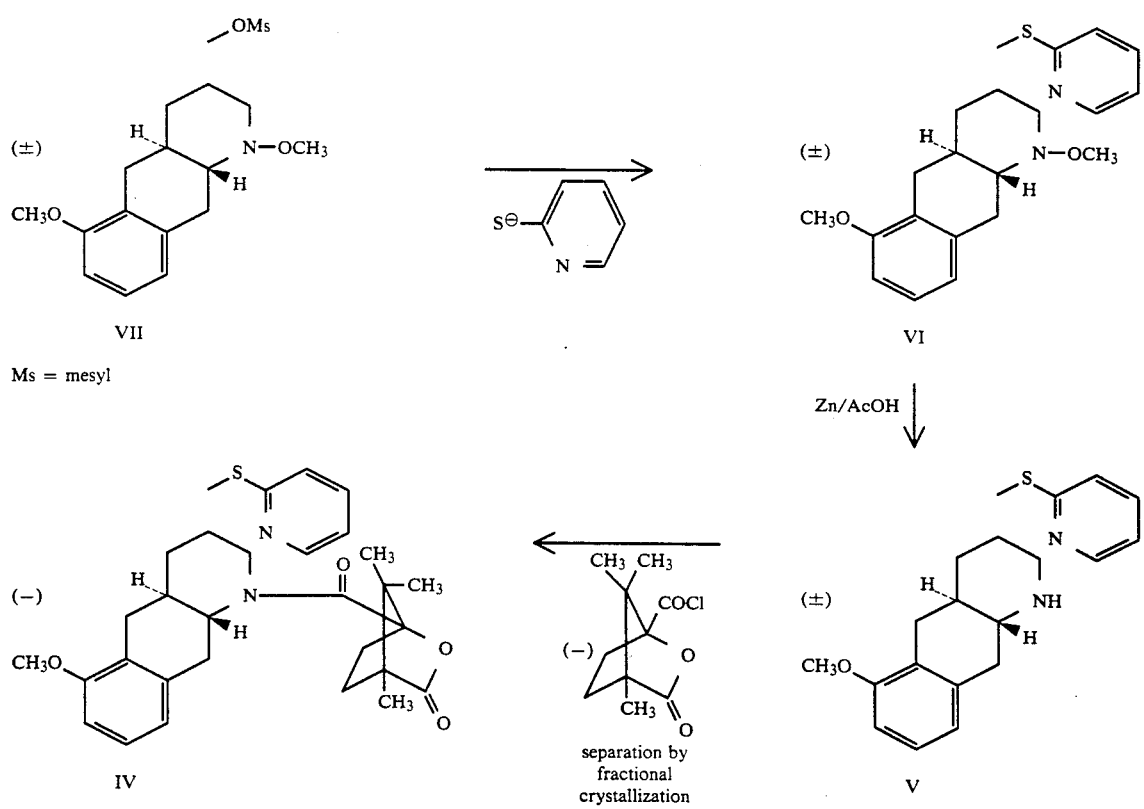

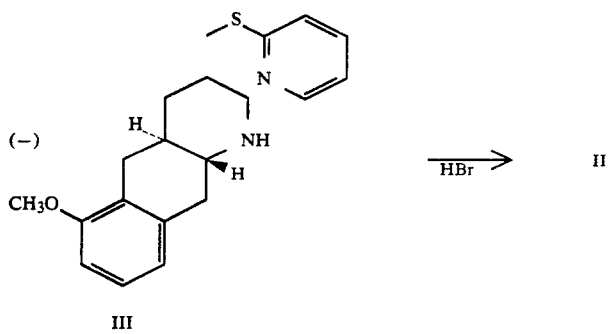

The starting compound of formula VII is known from literature.

The compound of formula I and its physiologically acceptable acid addition salts, referred to hereinafter as compounds according to the invention, exhibit interesting pharmacological activities in animal tests and may therefore be used as pharmaceuticals.

The compounds according to the invention have in particular dopaminergic activity in vivo on the central nervous system, which is detected by contralateral rotation when administered at doses of 1 to 20 mg/kg p.o. or 0.1 to 0.3 mg/kg s.c. to rats which have undergone unilateral lesions in the nigrostriatal dopamine tract through a 6-hydroxy-dopamine injection [U. Ungerstedt, Acta physiol. scand. Suppl. 367, 69–93 (1973)].

The compounds according to the invention can therefore be used as dopaminergic agents, e.g. in the treatment of Parkinson's disease.

Furthermore, the compounds according to the invention effect a decrease on the intraocular pressure in rabbits, at concentrations of 10 to 100 $\mu$M. Male rabbits of ca. 2 1/2 kg are fixed in cages leaving their heads free. The solutions with the compound to be tested are applied to the right eye and the placebo solutions to the left eye (2 drops each, i.e. ca. 40 $\mu$l). The eyes are firstly anaesthetized with a solution containing Novesine (0.4 %) and Fluorescein (0.05 %) and the ocular pressure is determined at various intervals after administration (10, 20, 30, 60, 90, 120, 180 and 240 minutes), whereby an applanation tonometer according to Goldberg is used.

The compounds according to the invention are therefore useful in the treatment of glaucoma.

The compounds according to the invention also show activity in the behavioural despair test [R.D. Porsolt et al., Arch. Int. Pharmacodyn., 229, 327–336 (1977)] upon administering doses of 100 mg/kg p.o.

The compounds for Lise according to the invention are therefore useful as antidepressants.

In addition, the compounds according to the invention effect an inhibition of the dependency on cocaine when administered at doses of 0.1 to 10 mg/kg p.o. to monkeys which administer the drug themselves according to the method described in Psychopharmacologia (Berl.) 16, 30–48 (1969).

The compounds according to the invention may therefore be used in the prevention, reduction or treatment of dependency (or for treatment after deprivation to avoid renewed dependency) arising from the abuse of cocaine.

For these therapeutical activities, the appropriate dosage varies and depends for example on the compound used, the species, the type of administration and the type and severity of the conditions to be treated. In general, satisfactory results are to be expected on animals receiving daily doses of ca. 0.1 to 50 mg/kg. With larger mammals, e.g. humans, an indicated daily dosage lies in the range ca. 1 to 100 mg, especially ca. 10 to 80 mg, of the compound according to the invention, which is conveniently administered e.g. in part doses up to 4 times daily.

The compounds according to the invention may be administered in any usual manner, e.g. orally, for example in the form of tablets or capsules, or parenterally, for example in the form of injection solutions or suspensions.

For the treatment of glaucoma, the compounds according to the invention are preferably applied topically to the eye in ca. 0.002 to ca. 0.02 % ophthalmological solutions.

The ophthalmic vehicle is such that the compound is maintained in contact with the ocular surface for a sufficient time period to allow the compound to penetrate the corneal and internal regions of the eye.

The pharmaceutically acceptable oplithalmic vehicle may be e.g. an ointment, vegetable oil, or an encapsulating material.

The compound of formula I is suitably administered in form of its hydrochloride.

In the above-mentioned test according to Ungerstedt, the compound of formula I in hydrochloride form induces about 1700 rotations within 7 hours at 0.1 mg/kg s.c.

In the above-mentioned intraocular pressure (IOP) test, the compound of formula I in hydrochloride form. reduces IOP in normal rabbits to the same extent as the standard $\beta$-blocker Timolol, however at 100 to 1000 fold lower molar concentrations, which is of particular interest with respect to side effects. Thus at concentrations of 10 to 100 $\mu$M, the maximum decrease is observed between 90 and 120 minutes after application and amounts 3.5 to 6 mm Hg (Timolol at 16 mM reduces IOP with a maximum of 2.5 to 3.5 mm Hg).

In the above-mentioned behavioural despair test, after administration of the compound of formula I in hydrochloride form at 0.1 to 0.3 mg/kg s.c., the decrease of the immobility time is about 35 %.

The present invention also provides pharmaceutical compositions comprising a COMPOLind according to the invention in association with at least one pharmaceutical carrier or diluent. Such compositions may be manufactured in conventional manner. Unit dosage forms contain, for example, from about 0.25 mg to about 50 mg of a compound according to this invention.

The present invention furthermore provides a method of treating glaucoma, depression, Morbus Parkinson or cocaine abuse in a subject in need of such treatment, which comprises administering a therapeutically effective amount of a compound according to the invention.

In the following example, all temperatures are uncorrected and are in degrees Centigrade.

EXAMPLE (−)-(3β,4aα,10aβ)-1,2,3,4,4a,5,10,10a-octahydro-3-[(2-pyridylthio)methyl]-1-methyl-6-hydroxy-benzo[g]quinoline a)

(±)-(3β,4aα,10aβ)-1,2,3,4,4a,5,10,10a-octahydro-3-[(2-pyridyl thio)methyl]-1,6-dimethoxy-benzo[g]quinoline A solution of 11 g (30.9 MM) of (±)-(3β,4aα,10aβ)-1,2,3,4,4a,5,10,10a-octahydro -3mesyloxymethyl-1,6-dimethoxybenzo[g]quinoline and 11 g (100 mill) of 2-mercaptopyridine in 200 ml of dimethylformamide is mixed at 10°–15° with 41 ml of 2N NaOH and stirred at room temperature for 20 hours. The suspension is worked by by concentrating in a rotary evaporator, mixing with water and extracting with methylene chloride. The organic phases are dried over Na2SO4, filtered and concentrated. Chromatography on silical gel with methylene chloride/3% ethanol yields 5.6 g of the title compound (49% of theory).

NMR (CDCl3, 360 MHz) δ0.94 (q, J=12 Hz, H-C9$_{ax}$), 2.74 (dd, J$_1$=12 Hz, J$_2$=18 Hz, H-C5$_{ax}$), 3.61 (s, N-OCH3), 3.8 (s, C-OCH3).

b)

(±)-(3,4aα,10aβ)-1,2,3,4,4a,5,10,10a-octahydro-3-1(2-pyridylthio)methyl]-6-methoxy-benzo[g]quinoline 10 g (27 mM) of the compound obtained under a) and 37.8 g (570 mill) of zinc are suspended in a solution of 55 ml of water and 110 ml of acetic acid and stirred at room temperature for 20 hours. The suspension is filtered through Hyflo, concentrated, adjusted to pH 7–8 with 2N NAOH and extracted with methylene chloride. After drying over Na2SO4, filtering and concentrating on a rotary evaporator, 8 g of crude product are obtained as a yellow oil, and this is chromatographed on silica gel with methylene chloride/2.5% methanol: 4.6 g of the title compound (50% of theory) are thereby obtained as a yellowish oil.

NMR (CDCl3, 360 MHz) δ1.03 (q, J =12 Hz, H-C9$_{ax}$), 2.67 (t,J=12, H-C5$_{ax}$), 2.88 (b, N—H), 3.8 (s, C—OCH3).

c)

(−)-(3β,4aα,10aβ)-1,2,3,4,4a,5,10,10a-octahydro-3-[(2-pyridylthio)methyl ]-6-methoxy-benzo[g]quinoline In order to split the racemate, the racemic sec. amine obtained under b) is converted using (−)-camphanic acid chloride into the two diastereoisomeric amides, which are separated by fractional crystallization from diisopropyl ether. The two diastereoisomeric amides possess the following rotational values (CHCl3): [α]$_D^{20}$ =−108° resp. [α]$_D^{20}$=+86° . In order to carry out amide hydrolysis, 3.4 g (6.5 mM) of the amide with [α]$_D^{20}$=−108° are stirred for 16 hours at 105° in 135 ml of conc. HCl, diluted with water, neutralized at 10° with 10 N NAOH and extracted with methylene chloride/10% isopropanol. The organic phases are dried with Na2SO4, filtered and concentrated on a rotary evaporator. The yield is 2 g of crude product, which is chromatographed on silica gel with methylene chloride/7% methanol. The resulting 1.6 g of pure enantiomer are used further without characterization.

d)

(−)-(3β,4aα,10aβ)-1,2,3,4,4a,5,10,10a-octahydro-3-[(2-pyridylthio)methyl]-6-hydroxy-benzo[g]quinoline 1.6 g (4.7 mill) of the pure enantiomer obtained under c) in 14 ml of HBr (47%) are stirred for 6 hours at 100° . The mixture is subsequently concentrated, neutralized with 2 N NAOH and extracted with methylene chloride/10% isopropanol. After drying over Na2SO4, filtering and concentrating by evaporation, 1.8 g of crude hydroxy derivative are obtained, which is chromatographed on silica gel with methylene chloride/7% metlianol. The resulting 1 g of pure hydroxy derivative is immediately N-methylated.

e)

(−)-(3β,4aα,10aβ)-1,2,3,4,4a,5,10,10a-octahydro-3-[(2-pyridylthio)methyl]-1-methyl-6-hydroxy-benzo[g]quinoline A solution of 1 g (3.06 mill) of the hydroxy derivative obtained under d) and 8 ml of aqueous 35% formaldehyde solution in 80 ml of methanol is stirred for 30 minutes at room temperature, and subsequently mixed slowly in portions at 0° with 2.2 g of NaBH4. After stirring for 2 hours at room temperature, it is concentrated, mixed with NaHCO3 solution and extracted with chloroform. Drying over Na2SO4, filtering and concentrating by evaporation yield 1 g (99% of theory) of pure title compound, which is crystallized from acetone/ethyl acetate: [α]$_D^{20}$=−162° (pyridine). Following recrystallization from acetone/ethyl acetate: [α]$_D^{20}$=−160° (pyridine). M.p. =186°–187°.

What we claim is:

1. The (−)-(3β,4a10,aβ)-1,2,3,4,4a,5,10,10a-octahydro-3-[(2-pyridylthio)methyl]-1-methyl-6-hydroxy-benzo[g]quinoline of formula I

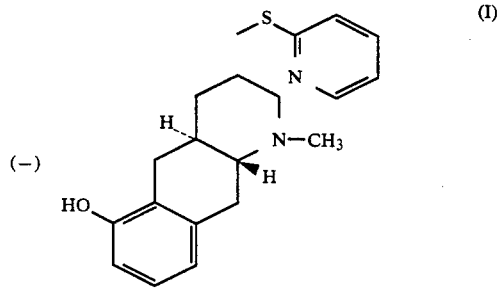

in free base form or in pharmaceutically acceptable acid addition salt form.

2. The compound of claim 1 in free base form.

3. The compound of claim 1 in form of the hydrochloride.

4. A pharmaceutical composition comprising a compound according to claim 1 in physiologically acceptable form, in association with a pharmaceutical carrier or diluent.

5. A method of treating glaucoma in a subject in need of such treatment, which comprises administering a therapeutically effective amount of a compound of claim 1 in pharmaceutically acceptable form.

6. A method of treating depression, Morbus Parkinson or cocaine abuse in a subject in need of such treatment, which comprises administering a therapeutically effective amount of a compound of claim 1 in pharmaceutically acceptable form.

* * * * *